United States Patent
Lacey et al.

(10) Patent No.: US 11,684,064 B2
(45) Date of Patent: Jun. 27, 2023

(54) CRYOGENIC VIAL ASSEMBLIES

(71) Applicant: Corning Incorporated, Corning, NY (US)

(72) Inventors: William Joseph Lacey, North Andover, MA (US); Gregory Roger Martin, Acton, ME (US); Allison Jean Tanner, Portsmouth, NH (US)

(73) Assignee: CORNING INCORPORATED, Corning, NY (US)

( * ) Notice: Subject to any disclaimer, the term of this patent is extended or adjusted under 35 U.S.C. 154(b) by 846 days.

(21) Appl. No.: 15/774,883

(22) PCT Filed: Nov. 3, 2016

(86) PCT No.: PCT/US2016/060310
§ 371 (c)(1),
(2) Date: May 9, 2018

(87) PCT Pub. No.: WO2017/087178
PCT Pub. Date: May 26, 2017

(65) Prior Publication Data
US 2018/0242573 A1    Aug. 30, 2018

Related U.S. Application Data

(60) Provisional application No. 62/255,633, filed on Nov. 16, 2015.

(51) Int. Cl.
*B01L 3/00*  (2006.01)
*A01N 1/02*  (2006.01)
*C12M 1/00*  (2006.01)

(52) U.S. Cl.
CPC .......... *A01N 1/0268* (2013.01); *B01L 3/5082* (2013.01); *B01L 3/50825* (2013.01);
(Continued)

(58) Field of Classification Search
CPC .. A01N 1/0268; C12M 45/22; B01L 3/50825; B01L 3/5082; B01L 2200/141;
(Continued)

(56) References Cited

U.S. PATENT DOCUMENTS

| 2,157,476 A | 5/1939 | Brodesser |
| 2,434,505 A | 1/1948 | Miller |

(Continued)

FOREIGN PATENT DOCUMENTS

| AU | 2010241296 B2 | 9/2014 |
| CA | 2314658 A1 | 1/2002 |

(Continued)

OTHER PUBLICATIONS

EP16808832.6 Office Action dated Jun. 9, 2020; 11 Pages; European Patent Office.
(Continued)

*Primary Examiner* — Nathan A Bowers
(74) *Attorney, Agent, or Firm* — Michael G. Panian

(57) ABSTRACT

Vial assemblies comprise a tubular body and a cap, the cap including a first portion configured to abut a lip of an open end of the tubular body, a threaded portion configured to couple to threading on an internal surface of the tubular body, and a second portion protruding from the threaded portion and extending into a cavity of the tubular body. Methods for storing and removing frozen samples from such vial assemblies are also described.

10 Claims, 3 Drawing Sheets

(52) U.S. Cl.
CPC ........ *C12M 45/22* (2013.01); *B01L 2200/141* (2013.01); *B01L 2300/042* (2013.01); *B01L 2300/043* (2013.01); *B01L 2300/046* (2013.01); *B01L 2300/0609* (2013.01); *B01L 2300/0832* (2013.01); *B01L 2300/0858* (2013.01); *B01L 2300/123* (2013.01)

(58) Field of Classification Search
CPC ......... B01L 2300/042; B01L 2300/043; B01L 2300/123; B01L 2300/0832; B01L 2300/0858; B01L 2300/046
See application file for complete search history.

(56) References Cited

U.S. PATENT DOCUMENTS

| | | |
|---|---|---|
| 2,992,501 A | 7/1961 | Douglas |
| 3,139,208 A | 6/1964 | Irwin et al. |
| 3,166,221 A | 1/1965 | Helmuth |
| 3,419,179 A | 12/1968 | Fritz et al. |
| 3,483,908 A | 12/1969 | Donovan |
| 3,491,907 A | 1/1970 | Eelkema |
| 3,727,802 A | 4/1973 | Schnurmacher |
| 3,810,503 A | 5/1974 | Lewis et al. |
| 3,827,602 A | 8/1974 | Nicholls |
| 4,018,222 A | 4/1977 | McAleer et al. |
| 4,251,995 A | 2/1981 | Pert et al. |
| 4,560,535 A | 12/1985 | Bouchee |
| 4,639,250 A | 1/1987 | Rycroft |
| 4,880,125 A | 11/1989 | LeBeau |
| 4,972,969 A | 11/1990 | Randklev |
| 5,033,631 A | 7/1991 | Nightingale |
| 5,699,935 A | 12/1997 | Stahley |
| 5,711,446 A | 1/1998 | Jeffs et al. |
| 5,826,751 A | 10/1998 | Stahley et al. |
| 5,873,490 A | 2/1999 | Walpole |
| 6,315,171 B1 | 11/2001 | Piscopo et al. |
| 6,337,205 B1 | 1/2002 | Wisniewski |
| 6,379,342 B1 | 4/2002 | Levinson |
| 6,446,860 B1 | 9/2002 | Robichaud |
| 8,092,878 B2 | 1/2012 | Miller et al. |
| 8,168,138 B2 | 5/2012 | Che et al. |
| 8,222,027 B2 | 7/2012 | Woods et al. |
| 8,550,273 B2 | 10/2013 | Levin et al. |
| 8,834,014 B2 | 9/2014 | Summons et al. |
| 2002/0056716 A1 | 5/2002 | Banhagel |
| 2002/0197656 A1 | 12/2002 | Li et al. |
| 2003/0175167 A1 | 9/2003 | Takanori et al. |
| 2004/0097862 A1 | 5/2004 | Lampeter et al. |
| 2004/0217080 A1 | 11/2004 | Renz |
| 2005/0124965 A1 | 6/2005 | Haywood |
| 2005/0155440 A1 | 7/2005 | Kanjilal et al. |
| 2006/0019233 A1 | 1/2006 | Yaghmour |
| 2008/0118686 A1 | 5/2008 | Glasgow et al. |
| 2009/0194904 A1 | 8/2009 | Logel et al. |
| 2009/0236258 A1 | 9/2009 | Connell |
| 2009/0255938 A1 | 10/2009 | Fuja |
| 2009/0305224 A1 | 12/2009 | He et al. |
| 2010/0196873 A1 | 8/2010 | Woods |
| 2010/0241074 A1 | 9/2010 | Bivin et al. |
| 2010/0316446 A1 | 12/2010 | Runyon |
| 2011/0008908 A1 | 1/2011 | Biesbrouck |
| 2011/0143452 A1 | 6/2011 | Che et al. |
| 2011/0174814 A1 | 7/2011 | Ortiz et al. |
| 2011/0250632 A1 | 10/2011 | Tatnell et al. |
| 2011/0295212 A1 | 12/2011 | Greter et al. |
| 2012/0027895 A1 | 2/2012 | Bach |
| 2012/0029471 A1 | 2/2012 | Lee et al. |
| 2012/0258214 A1 | 10/2012 | Sagel |
| 2013/0065301 A1 | 3/2013 | Woods et al. |
| 2014/0079898 A1 | 3/2014 | Kaushik et al. |
| 2014/0138406 A1 | 5/2014 | Sanfilippo et al. |
| 2014/0157798 A1 | 6/2014 | Jimenez-Rios et al. |
| 2014/0158695 A1 | 6/2014 | Jimenez-Rios |
| 2014/0224808 A1 | 8/2014 | Brisard |
| 2015/0048085 A1 | 2/2015 | Brown et al. |
| 2016/0031611 A1 | 2/2016 | Kranz et al. |
| 2016/0363362 A1 | 12/2016 | Chen et al. |
| 2017/0172140 A1 | 6/2017 | Schaefer |
| 2018/0242572 A1 | 8/2018 | Coddaire et al. |
| 2018/0242573 A1 | 8/2018 | Lacey et al. |

FOREIGN PATENT DOCUMENTS

| | | |
|---|---|---|
| CH | 240683 A | 1/1946 |
| CN | 2892068 Y | 4/2007 |
| CN | 201284338 Y | 8/2009 |
| CN | 201322489 Y | 10/2009 |
| CN | 102379278 A | 3/2012 |
| CN | 202522460 U | 11/2012 |
| CN | 203290150 U | 11/2013 |
| CN | 203519403 U | 4/2014 |
| CN | 204599132 U | 9/2015 |
| CN | 104986426 A | 10/2015 |
| DE | 102012025254 A1 | 6/2014 |
| EP | 1346773 A2 | 9/2003 |
| EP | 2191899 A1 | 6/2010 |
| EP | 2364928 A1 | 9/2011 |
| EP | 2575442 A1 | 4/2013 |
| EP | 2442857 B1 | 8/2016 |
| FR | 1411842 A | 9/1965 |
| FR | 2846128 A1 | 4/2004 |
| JP | 07-333219 A | 12/1995 |
| JP | 10-309185 A | 11/1998 |
| JP | 2000516137 A | 12/2000 |
| JP | 2001106262 A | 4/2001 |
| JP | 2003267463 A | 9/2003 |
| JP | 2004018504 A | 1/2004 |
| JP | 2006516398 A | 7/2006 |
| JP | 2008-507563 A | 3/2008 |
| JP | 2010-518393 A | 5/2010 |
| JP | 04848755 B2 | 12/2011 |
| JP | 04876922 B2 | 2/2012 |
| JP | 2012020763 A | 2/2012 |
| JP | 2012-219017 A | 11/2012 |
| JP | 2014-190904 A | 10/2014 |
| WO | 9901770 A1 | 1/1999 |
| WO | 0030703 A1 | 6/2000 |
| WO | 01/43869 A2 | 6/2001 |
| WO | 200228733 A1 | 4/2002 |
| WO | 2005022996 A1 | 3/2005 |
| WO | 2006012613 A1 | 2/2006 |
| WO | 2006059626 A1 | 6/2006 |
| WO | 2007103917 A2 | 9/2007 |
| WO | 2008/097091 A1 | 8/2008 |
| WO | 2010/145786 A1 | 12/2010 |
| WO | 2011146998 A1 | 12/2011 |
| WO | 2013171483 A1 | 11/2013 |
| WO | 2014/095840 A1 | 6/2014 |
| WO | 2014088859 A1 | 6/2014 |
| WO | 2015/023560 A2 | 2/2015 |
| WO | 2016040063 A1 | 3/2016 |
| WO | 2017/087178 A1 | 5/2017 |
| WO | 2017087176 A1 | 5/2017 |

OTHER PUBLICATIONS

Japanese Patent Application No. 2018-525340; Notice of Reasons for Refusal dated Oct. 7, 2020; 10 pages; Japanese Patent Office.
International Search Report and Written Opinion of the International Searching Authority; PCT/US2016/060310; dated Apr. 5, 2017; 17 pages; European Patent Office.
Invitation to Pay Additional Fees of the International Searching Authority; PCT/US2016/060310; dated Feb. 8, 2017; 8 pages; European Patent Office.
Corning 1.2mL External Threaded Polypropylene Cryogenic Vial, Self-Standing With Conical Bottom (Product #430658) Corning Life Sciences Catalong, Jan. 24, 2015, https://catalog2.corning.com/LifeSciences/en-US/Shopping/ProductDetails.aspx?productid=430658.
English Translation of CN201680066888.6 Office Action dated Jul. 29, 2020; 8 pages; Chinese Patent Office.

(56) References Cited

OTHER PUBLICATIONS

European Patent Application No. 22208527.6, Extended European Search Report, dated Feb. 10, 2023; 8 pages; European Patent Office.

CRYOGENIC VIAL ASSEMBLIES

This is a national stage application under 35 U.S.C. § 371 of International Application No. PCT/US2016/060310, filed on Nov. 3, 2016, which claims the benefit of priority under 35 U.S.C. § 119 of U.S. Provisional Application Ser. No. 62/255,633 filed on Nov. 16, 2015 the content of which is relied upon and incorporated herein by reference in its entirety.

FIELD OF THE DISCLOSURE

The present disclosure relates generally to cryopreseravation devices, and more specifically to cryogenic vial assemblies for preparing and storing frozen samples, and methods for removing frozen samples from such vial assemblies.

BACKGROUND

Biological samples such as cells and tissues are often cryopreserved to extend their viability and usefulness for a variety of applications. For example, the cryopreservation process can involve placing a biological sample into an aqueous solution containing electrolytes and/or cryoprotectants and lowering the temperature of the solution to below its freezing point. Biological samples are often stored in vials which can be sealed and frozen, e.g., by immersion in liquid nitrogen. It can be important to maintain the sample integrity during the filling, storage, and retrieval stages, as contamination can render a biological sample useless for scientific research or other applications.

Vial leakage, which can be caused by a failure of the seal between the vial and the cap, can be a contributing factor to sample contamination. Sample contamination can also occur during thawing of the sample prior to its removal from the vial. For instance, cryogenic vials are often placed in a warm bath or heated block to partially or completely defrost the sample for ease of removal. However, samples can become contaminated or lose part of their viability during this process due to liquid immersion and/or elevated temperatures. The sample may also become overstressed due to excessive heating at the vial wall surface which can further damage the sample.

Removal of samples in the frozen state without thawing may reduce the risk of sample contamination and/or damage. However, it can be difficult to remove the frozen pellet from the vial due to adhesion of the sample to the vial walls and/or inability to grip and/or exert a force on the sample. Accordingly, it would be advantageous to provide vial assemblies from which frozen samples can be more easily discharged while also maintaining an acceptable seal integrity for preventing sample contamination. It would also be advantageous to provide methods for preparing frozen samples which can be more easily discharged from a vial and methods for removing frozen samples from vials without the need for thawing prior to removal.

SUMMARY

The disclosure relates, in various embodiments, to vial assemblies comprising a tubular body comprising a cavity, an open end comprising a lip, and a closed end, wherein an internal surface of the tubular body proximate the open end comprises threading; and a cap configured to couple to the open end of the tubular body, wherein the cap comprises (a) a first portion configured to abut the lip of the open end; (b) a threaded portion configured to couple to at least a portion of the threading on the internal surface of the tubular body; and (c) a second portion protruding from the threaded portion and extending into the cavity of the tubular body.

Also disclosed herein are methods for preparing and storing frozen samples in a vial assembly, the methods comprising introducing a liquid sample into a cavity of a tubular body; engaging an open end of the tubular body with a cap to form a sealed vial assembly, wherein the cap comprises a first portion configured to abut a lip of the open end of the tubular body, a threaded portion configured to couple to at least a portion of threading on an internal surface of the tubular body, and a second portion protruding from the threaded portion and extending into the cavity of the tubular body, wherein when the cap is engaged with the open end of the tubular body the second portion of the cap is at least partially immersed in the liquid sample; and freezing the sealed vial assembly.

Further disclosed herein are methods for removing frozen samples from a vial assembly comprising a tubular body and a cap, the methods comprising rotating the cap of the vial assembly to disengage a threaded portion of the cap from threading on an internal surface of the tubular body, wherein rotating the cap causes a second portion of the cap in physical contact with the frozen sample to rotate the frozen sample and at least partially disengage the frozen sample from the internal surface of the tubular body; removing the cap; and removing the frozen sample from the vial assembly.

Vial assemblies disclosed herein may provide a user with the ability to loosen and remove a frozen sample from a vial without thawing the sample beforehand. Methods for removing frozen samples from the vial assemblies disclosed herein may have improved consistency and/or repeatability, thereby saving the user time and/or decreasing variability from sample to sample due to varying sample removal conditions, e.g., differing time and/or temperature used to thaw a sample. It should be noted, however, that one or more of such benefits may not be present according to various embodiments of the disclosure, yet such embodiments are intended to fall within the scope of the disclosure.

The disclosure provides, in an aspect (1), a vial assembly comprising: a tubular body comprising a cavity, an open end comprising a lip, and a closed end, wherein an internal surface of the tubular body proximate the open end comprises threading; and a cap configured to couple to the open end of the tubular body, wherein the cap comprises: a first portion configured to abut the lip of the open end; a threaded portion configured to couple to at least a portion of the threading on the internal surface of the tubular body; and a second portion protruding from the threaded portion and extending into the cavity of the tubular body. In an aspect (2), the disclosure provides the vial assembly of aspect 1, wherein the cap is configured to couple to the open end of the tubular body by rotation to engage the threaded portion of the cap to the threading on the internal surface of the tubular body. In an aspect (3), the disclosure provides the vial assembly of aspect 1 or 2, wherein the tubular body comprises a first portion having an internal surface comprising threading and a second portion having an internal surface not comprising threading. In an aspect (4), the disclosure provides the vial assembly of any one of aspects 1-3, wherein a diameter of the first portion of the tubular body is greater than a diameter of the second portion of the tubular body. In an aspect (5), the disclosure provides the vial assembly of any one of aspects 1-4, wherein the internal surface of the tubular body comprising threading extends from the open end to the closed end of the tubular body. In an aspect (6), the disclosure provides the vial assembly of any one of aspects 1-5, wherein the first portion comprises an upper portion having a height extending above the lip of the open end, the upper portion comprising a textured surface. In an aspect (7), the disclosure provides the vial assembly of any one of aspects 1-6, wherein the first portion is configured to seal the open end of the tubular body. In an aspect (8), the disclosure provides the vial assembly of any one of aspects 1-7, further comprising a sealing member between the first portion and the lip of the tubular body. In an aspect (9), the disclosure provides the vial assembly of any one of aspects 1-8, wherein the threaded portion of the cap comprises a hollow cylinder having an external threaded surface. In an aspect (10), the disclosure provides the vial assembly of any one of aspects 1-9, wherein the second portion comprises a substantially flat piece having at least one dimension chosen from length or width greater than a thickness of the substantially flat piece. In an aspect (11), the disclosure provides the vial assembly of aspect 10, wherein the second portion comprises at least one aperture extending across the thickness of the second portion. In an aspect (12), the disclosure provides the vial assembly of any one of aspects 1-11, wherein the tubular body comprises a tube wall and wherein at least a first portion of the tube wall proximate the closed end has a thickness less than a thickness of a second portion of the tube wall proximate the open end. In an aspect (13) the disclosure provides the vial assembly of aspect 12, further comprising at least two flanges proximate the closed end of the tubular body, wherein the flanges are configured to hinge inwardly and apply force to the closed end of the tubular body. In an aspect (14), the disclosure provides the vial assembly of aspect 13, wherein the flanges further comprise at least one gusset configured to apply an upward force to the closed end of the tubular body.

In a further aspect (15), the disclosure provides a method for preparing a frozen sample, comprising: introducing a liquid sample into a cavity of a tubular body; engaging an open end of the tubular body with a cap to form a sealed vial assembly, wherein the cap comprises: a first portion configured to abut a lip of the open end of the tubular body; a threaded portion configured to couple to at least a portion of threading on an internal surface of the tubular body; and a second portion protruding from the threaded portion and extending into the cavity of the tubular body; wherein when the cap is engaged with the open end of the tubular body the second portion of the cap is at least partially immersed in the liquid sample; and freezing the sealed vial assembly. In an aspect (16), the disclosure provides the method of aspect 15, wherein engaging the open end of the tubular body with the cap comprises rotating the cap to engage the threaded portion of the cap to the threading on the internal surface of the tubular body. In an aspect (17), the disclosure provides the method of aspect 15, wherein the liquid sample comprises a biological sample. In an aspect (18), the disclosure provides a method for removing a frozen sample from a vial assembly comprising a tubular body and a cap, the method comprising: rotating the cap of the vial assembly to disengage a threaded portion of the cap from threading on an internal surface of the tubular body; wherein rotating the cap causes a second portion of the cap in physical contact with the frozen sample to rotate the frozen sample and at least partially disengage the frozen sample from the internal surface of the tubular body; removing the cap; and removing the frozen sample from the vial assembly. In an aspect (19) the disclosure provides the method of aspect 18, further comprising applying pressure to at least a portion of a closed end of the tubular body, wherein the closed end is configured to compress at least partially upon the application of pressure. In an aspect (20), the disclosure provides the method of aspect 19, wherein applying pressure to at least a portion of the closed end of the tubular body comprises depressing two or more flanges proximate the closed end. In an aspect (21), the disclosure provides the method of aspect 19, wherein the frozen sample is at least partially attached to the second portion of the cap and removing the frozen sample comprises pulling the cap from the tubular body for a distance sufficient to fully disengage the frozen sample from the tubular body. In an aspect (22), the disclosure provides the method of aspect 19, wherein the threading on the internal surface of the tubular body extends from the open end to the closed end of the tubular body and wherein removing the frozen sample comprises rotating the cap for a number of revolutions sufficient to disengage the frozen sample from the threading of the tubular body.

Additional features and advantages of the invention will be set forth in the detailed description which follows, and in part will be readily apparent to those skilled in the art from that description or recognized by practicing the invention as described herein, including the detailed description which follows, the claims, and the appended drawings.

It is to be understood that both the foregoing general description and the following detailed description present various embodiments of the disclosure, and are intended to provide an overview or framework for understanding the nature and character of the claims. The accompanying drawings are included to provide a further understanding of the disclosure, and are incorporated into and constitute a part of this specification. The drawings illustrate various embodiments of the disclosure and together with the description serve to explain the principles and operations of the invention.

BRIEF DESCRIPTION OF THE DRAWINGS

The following detailed description can be best understood when read in conjunction with the following drawings, in which.

DETAILED DESCRIPTION

Vial Assemblies

Disclosed herein are vial assemblies comprising a tubular body comprising a cavity, an open end comprising a lip, and a closed end, wherein an internal surface of the tubular body proximate the open end comprises threading; and a cap configured to couple to the open end of the tubular body, wherein the cap comprises (a) a first portion configured to abut the lip of the open end; (b) a threaded portion configured to couple to at least a portion of the threading on the internal surface of the tubular body; and (c) a second portion protruding from the threaded portion and extending into the cavity of the tubular body.

Embodiments of the disclosure will be discussed with reference to FIGS. 1-4, which illustrate various aspects of a vial assembly according to non-limiting embodiments of the disclosure. The following general description is intended to provide an overview of the claimed apparatus and various aspects will be more specifically discussed throughout the disclosure with reference to the non-limiting embodiments, these embodiments being interchangeable with one another within the context of the disclosure.

Figure 1A:
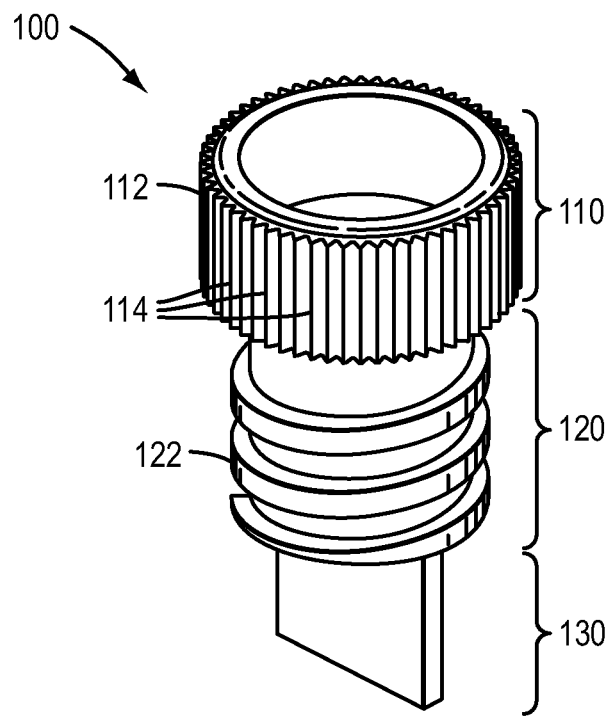
FIGS. 1A-B are perspective views of a vial cap according to embodiments disclosed herein.
Figure 1B:
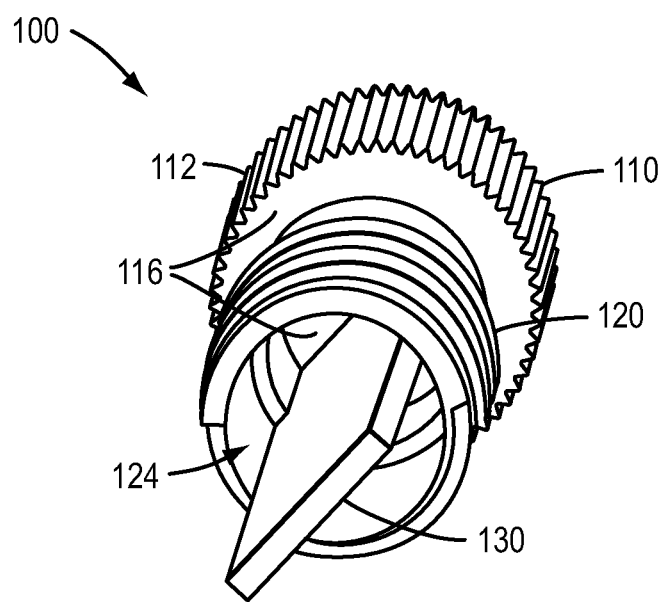

As demonstrated in FIGS. 1A-B, which are perspective views of the side and bottom of a vial cap according to various embodiments of the disclosure, respectively, a vial assembly can comprise a cap 100 including a first portion 110, a threaded portion 120, and a second portion 130. Various aspects of the cap will be discussed with reference to the vial to which the cap is configured to mate or couple. The vial can, in non-limiting embodiments, comprise a tubular body having a cavity, an open end, and a closed end, which is discussed in more detail with reference to FIG. 2.

The first portion 110 can, in various embodiments, be configured to abut a lip defining an opening of the tube or vial to be sealed. The open end of the tubular body can comprise an aperture having, for example, a substantially circular shape. The diameter of the first cap portion 110 can, in some embodiments, be substantially equal to the diameter of the aperture defined lip. According to such an embodiment, the first portion 110 of the cap can rest atop the lip to seal the opening. In other embodiments, the first portion 110 can have a diameter slightly larger than the diameter of the vial opening, such that the first portion surrounds the lip, e.g., fitting snugly around the vial lip to seal the opening.

In certain embodiments, the first portion 110 can comprise a bottom surface 116 configured to contact the vial lip, and an upper portion 112. The upper portion 112 can comprise an outer surface having one or more textural elements 114. For example, all or a portion of the outer surface may be textured to improve gripping ease when handling, closing, and/or opening the vial assembly. In certain embodiments, the outer surface of the upper portion 112 can be ribbed. According to additional embodiments, portions of the outer surface of the upper portion 112 can be textured, e.g., one or more regions of textured surface, such as strips or grips for finger placement.

The threaded portion 120 of the cap 100 can be contiguous with the first portion 110 and can comprise at least one threaded external surface 122 capable of mating or coupling with an internal surface of the tubular body. For example, at least a portion of the internal surface of the tubular body can comprise threading, which can match the threading on an external surface of the threaded portion 120 of the cap 100. As used herein, the terms "threaded" and "threading" and variations thereof are intended to denote alternating raised and recessed sections generally defining an upward or downward spiral motion, e.g., such that the cap can be screwed or rotated on and off the tubular body. Thus, at least a portion of the threaded portion 120 of the cap 100 can engage at least a portion of threading located on an internal surface of the tubular body such that the cap can be rotated or screwed on and off and/or tightened or loosened by a rotating motion.

According to various embodiments, the threaded portion 120 can comprise a hollow, substantially cylindrical shape having an opening 124. Such an opening may provide for additional volume in the vial for sample storage, e.g., a liquid sample can fill all or a portion of the hollow internal volume of the threaded portion. In other embodiments (not illustrated), the threaded portion 120 can be a solid cylindrical piece.

The second portion 130 can be contiguous with the first and/or threaded portion of the cap and can protrude from the second portion at least partially into a cavity defined by the tubular body (in which the sample is placed). In the case of a hollow threaded portion 120, as depicted in FIGS. 1A-B, the second portion 130 can be attached to the bottom surface 116 of the first portion 110, extending through the hollow threaded portion 120, and protruding from the threaded portion downward into the cavity of the vial. In other embodiments, such as in the case of a solid threaded portion 120, the second portion 130 can be attached to the threaded portion 120 and can protrude from the threaded portion into the cavity of the vial.

According to non-limiting embodiments, the second portion can have any shape. For example, the second portion can be flat or rounded, straight or curved, wavy, orthoganol or conical, just to name a few operative shapes. The second portion can have smooth or non-smooth surfaces. The bottom of the second portion can be flat or rounded. As shown in FIGS. 1A-B, the second portion 130 can have a substantially flat shape, such as a square or rectangular shape, and may have a length and/or width larger than its thickness. Of course other shapes and configurations, such as rounded shapes or edges, are envisioned as falling within the scope of the disclosure. According to various aspects, the second portion may be a solid piece and may not serve as a conduit into the cavity, such as a needle or other conduit for adding or removing samples from the cavity. In additional aspects, the second portion 130 may be substantially flat or planar, e.g., not concave or convex. In certain embodiments, the second portion 130 can be envisioned as a "key" that can engage a frozen sample in a manner similar to a flat screwdriver engaging a slot in the top of a screw. Or, for example, the second portion can have any three dimensional shape, such as an "X" shape, like a Philips-head screwdriver, or a star shape.

For instance, when liquid is added to the vial and the cap 100 is screwed on to seal the vial, the second portion 130 can be at least partially immersed or submerged in the liquid within the cavity. Upon freezing, the sample will form a complementary shape surrounding the second portion, such as a male/female pairing, e.g., a mated protrusion and a recess. Thus, when the frozen sample is to be removed, the rotating motion of the cap 100 can cause the second portion 130 to engage with the frozen sample and rotate the sample pellet within the vial.

By way of a non-limiting example, the second portion 130 can extend into the cavity to a distance equal to at least about 10% of the length of the cavity, such as at least about 20%, at least about 30%, at least about 40%, or at least about 50% of the cavity length, including all ranges and subranges therebetween. When the second portion 130 protrudes or extends further into the cavity, engagement between the second portion 130 and the frozen sample can be enhanced; however, the increased length can also result in less volume available for sample filling in the cavity. Similarly, a thicker piece can provide additional structural rigidity but likewise takes up additional space within the cavity. It is within the ability of one skilled in the art to weight these considerations when selecting a length, width, and/or thickness for the second portion 130. Non-limiting exemplary dimensions for the second portion may include, for example, a length and/or width ranging from about 0.25 cm to about 3 cm, such as from about 0.5 cm to about 2.5 cm, from about 0.75 cm to about 2 cm, or from about 1 cm to about 1.5 cm, including all ranges and subranges therebetween. Suitable thicknesses include, for instance, from about 0.05 cm to about 0.3 cm, such as from about 0.1 cm to about 0.25 cm, from about 0.125 cm to about 0.2 cm, or from about 0.1 cm to about 0.15 cm, including all ranges and subranges therebetween. Of course these dimensions can vary as desired or as appropriate depending e.g., on the size of the cryotube employed.

In additional embodiments, the second portion 130 or "key" can include one or more apertures or openings (not illustrated), such as a hole spanning its thickness. In these aspects, such an aperture can further engage the frozen pellet, e.g., a liquid sample can fill the aperture and solidify upon freezing to occupy the aperture and positively engage the second portion 130. Additional engagement between the frozen sample and the aperture can further provide a way to pull the sample from the vial or transport the sample after removal, as the pellet can remain engaged to the cap. Such an embodiment can reduce the risk of dropping the frozen sample during and/or after removal from the tube. It is to be understood that the aperture disclosed herein does not affect the seal of the vial assembly, e.g., it is not an aperture or opening providing access into the cavity when the assembly is in a closed position. The aperture is also distinguishable from an aperture spanning the length of the second portion, such as a conduit in a needle or other similar aperture.

Figure 2:
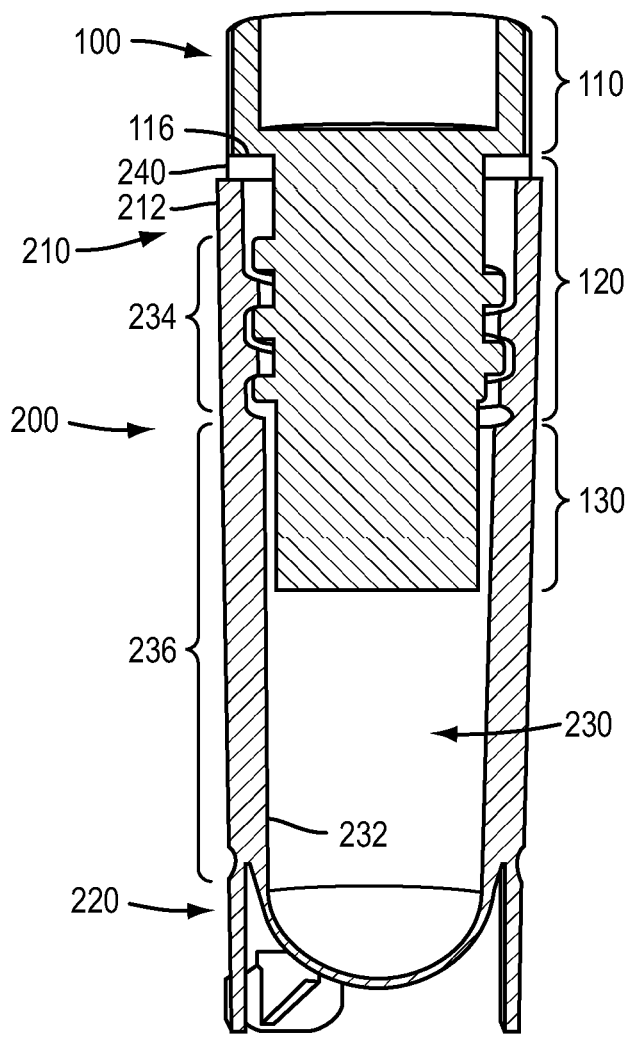
FIG. 2 is a cross-sectional view of a vial assembly according to various disclosed embodiments.

As depicted in FIG. 2, which is a cross-sectional view of an exemplary vial assembly, the apparatuses disclosed herein can comprise a tubular body or vial 200 comprising an open end 210, a closed end 220, and a cavity 230. The open end 210 can comprise a lip 212 defining the opening to be sealed by the cap 100. The lip 212 can engage, in some embodiments, the bottom surface 116 of the first portion 110 of the cap, such that in the closed position the bottom surface 116 abuts the lip 212. Optionally, a seal or sealing material 240 can be provided between the lip 212 and the bottom surface 116 to enhance the integrity of the seal. Suitable sealing materials can include, for example, thermoplastic and thermoset elastomers, such as silicon-based polymers (e.g., polydimethylsiloxane) or multi-block elastomer alloys (e.g., VERSAFLEX™ products from POLYONE, such as CL2250 or HC MT222), to name a few. In some embodiments, a sealing ring can be placed around the lip 212.

According to various aspects, the cavity 230 can comprise an internal surface 232. The internal surface 232 can comprise at least one threaded portion 234 proximate the open end 210 of the tubular body 200. The remainder of the internal surface extending down to the closed end 220 can comprise an unthreaded portion 236 according to certain non-limiting embodiments (as illustrated in FIG. 2). In other embodiments, although not illustrated, the threaded portion 234 can have a longer length or the entire internal surface 232 of the cavity 230 can be threaded. In still further aspects, when the cavity 230 comprises threaded and unthreaded portions, the diameter of the threaded portion 234 can be greater than the diameter of the unthreaded portion 236. For instance, the diameter of the threaded portion can be at least about 5% greater than the diameter of the unthreaded portion, such as at least about 10%, 15%, 20%, or 25% greater, including all ranges and subranges therebetween.

Such embodiments may promote the ease of removal of the frozen sample from the vial. In the case of a continuously threaded internal surface, the sample can be frozen into the grooves of the threading, thereby creating a complimentary threading on the surface of the frozen pellet, which can create a mechanism by which the frozen sample can be rotated out of the vial. Additionally, by threading the entire inner surface, potential issues associated with "undercutting" or obstruction of the sample upon removal may be avoided, as the sample having a diameter equal to that of the unthreaded portion need not pass through a slightly narrower threaded portion to exit the vial. In other embodiments, undercutting can be reduced or avoided by configuring the cavity to have an unthreaded portion and a threaded portion, wherein the unthreaded portion has a smaller diameter than the threaded portion. For example, the diameter of the unthreaded portion can be less than or equal to the inside diameter of the threaded portion at its narrowest point, e.g., the distance between two raised thread surfaces, as opposed to greater than or equal to the outside diameter of the threaded portion at its widest point, e.g., the distance between two recessed thread surfaces.

Figure 3:
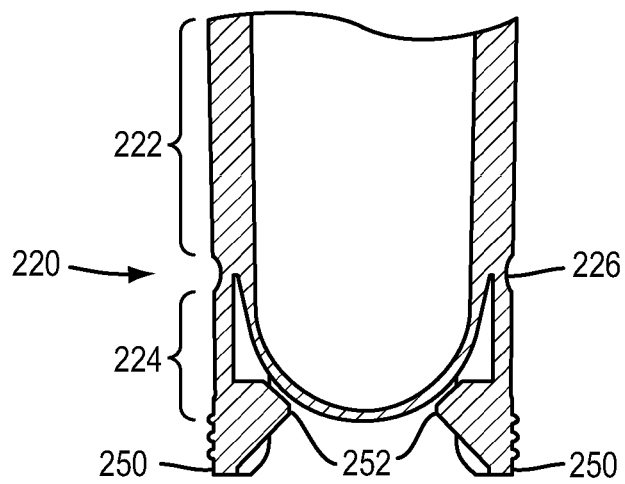
FIG. 3 is a cross-sectional view of the bottom of a vial assembly according to certain embodiments disclosed herein.

The closed end 220 of the tubular body 200 is illustrated in FIG. 3 and will be discussed in more detail with reference to this cross-sectional image. As depicted in FIG. 3, the closed end 220 can have a substantially rounded bottom 224, although other shapes are possible and envisioned as falling within the scope of the disclosure. The closed end can have substantially similar properties to the remainder of the tubular body, e.g., wall thickness, rigidity, etc. In other embodiments, and as illustrated in FIG. 3, the closed end 220 can be equipped with one or more features for promoting disengagement of the frozen sample from the vial. For instance, various portions of the closed end 220 can have a reduced wall thickness to enhance malleability of the tube in those locations. Whereas an upper portion 222 of the closed end 220 can have a thicker sidewall substantially matching the rest of the vial, the bottom region 224 of the closed end may have a reduced wall thickness, which may facilitate bending, flexing, and/or pinching of the tube in this location to encourage dislodgment of the frozen sample from the tube. For example, the closed end may be as described in co-pending and co-owned U.S. patent application Ser. No. 62/255,627.

In some embodiments, the vial assembly can be provided with additional side walls or flanges 250 attached to the tubular body 200 proximate the closed end 220. The flanges 250 can serve multiple functions, e.g., providing a stand for the vial and/or a means for storing the vial within a rack or stand. Additionally, the flanges 250 can be configured to bend inwardly upon application of force to apply pressure to the bottom 224 of the closed end 220. For instance, the flanges 250 may be used as a hinge to pinch or otherwise impinge on the bottom 224 of the closed end 220.

Further features may be added to the tubular body 200 and/or the flanges 250 to enhance the ability to dislodge the frozen sample from the vial. In some embodiments, the wall of the vial can be thinned in a second location 226 proximate the attachment point of the flange 250 to the tubular body 200. Thinning of the tube wall in this location may enhance the ability of the flanges 250 to hinge inwardly. Additionally, the flanges 250 can be equipped with gussets or inward protrusions 252 that can increase the force applied to the bottom 224 of the closed end 220. Force applied to the flanges 250 can be redirected by the gussets 252 to the bottom of the vial, e.g., providing an upward force pushing into the bottom of the vial to dislodge the pellet.

Figure 4:
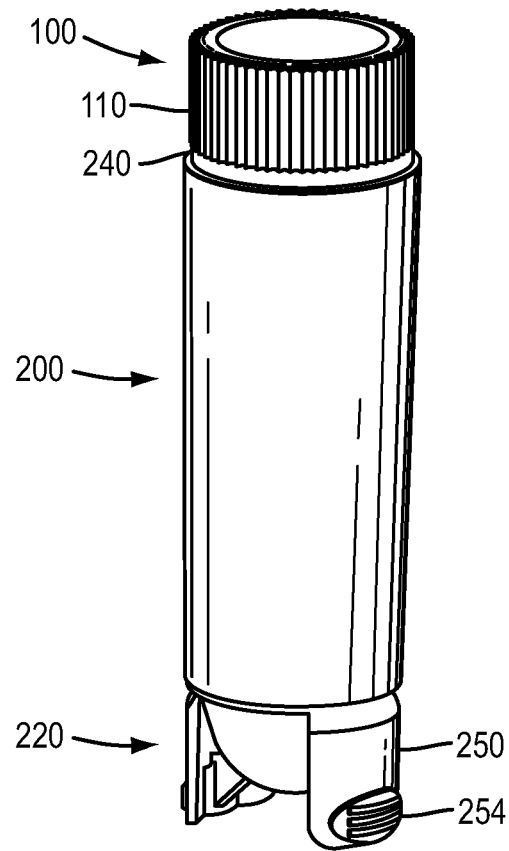
FIG. 4 is a perspective view of a vial assembly according to embodiments disclosed herein.

FIG. 4 illustrates a perspective view of the exterior of a vial assembly according to various aspects of the disclosure. In the closed position, the first portion 110 of the cap 100 is visible, which is engaged with the open end of the tubular body 200 via seal 240. The threaded portion and second portion of the cap 100 are located inside the cavity of the tubular body 200 and therefore not visible in the closed position. The closed end 220 of the tubular body 200 is optionally equipped with flanges 250 for standing the vial upright and/or for disengaging the frozen sample from the vial. The flanges 250 can, in some embodiments, include a textured region 254, which can be raised for enhanced gripping by a user during use (e.g., finger grips) and/or for insertion into a storage rack or block, or recessed for fitting into standard tube racks.

The vial assemblies, including the tubular bodies and caps thereof, can be manufactured from any materials suitable for cryopreservation applications. Non-limiting exemplary materials can include, for example, plastics such as polyolefins synthetic and thermoplastic polymers, such as polypropylene, polyethylene, polystyrene, polyester, polycarbonate, and polytetrafluoroethylene, to name a few. According to various embodiments, the tubular body and cap of the vial assembly can comprise the same or different materials. Additionally, the cap may comprise a substantially rigid material, whereas the tube can comprise a rigid or flexible material. In certain embodiments, the tubular body can comprise a material which, at a sufficiently high thickness can provide rigidity at the open end, but at a sufficiently low thickness can provide flexibility at the closed end of the tube. For example, according to various embodiments, the thickness of the wall of the tubular body proximate the open end can range from about 0.05 cm to about 0.2 cm, such as from about 0.06 cm to about 0.15 cm, or from about 0.075 cm to about 0.125 cm, including all ranges and subranges therebetween, whereas the thickness of the wall of the tubular body proximate the closed end can range from about 0.025 cm to about 0.1 cm, such as from about 0.03 cm to about 0.075 cm, from about 0.04 cm to about 0.07 cm, or from about 0.05 cm to about 0.06 cm, including all ranges and subranges therebetween.

Additional optional features can be included in the vial assembly disclosed herein, e.g. for improved ease of handling, heat transfer, and/or sealing of the vial.

Methods

Methods disclosed herein can include methods for preparing a frozen sample in a vial assembly and methods for removing a frozen sample from a vial assembly. Methods for preparing and/or storing frozen samples can include introducing a liquid sample into a cavity of a tubular body; engaging an open end of the tubular body with a cap to form a sealed vial assembly, wherein the cap comprises a first portion configured to abut a lip of the open end of the tubular body, a threaded portion configured to couple to at least a portion of threading on an internal surface of the tubular body, and a second portion protruding from the threaded portion and extending into the cavity of the tubular body, wherein when the cap is engaged with the open end of the tubular body the second portion of the cap is at least partially immersed in the liquid sample; and freezing the sealed vial assembly. Methods for removing frozen samples from a vial assembly can include rotating the cap of the vial assembly to disengage a threaded portion of the cap from threading on an internal surface of the tubular body, wherein rotating the cap causes a second portion of the cap in physical contact with the frozen sample to rotate the frozen sample and at least partially disengage the frozen sample from the internal surface of the tubular body; removing the cap; and removing the frozen sample from the vial assembly. Of course, it is to be understood that the features disclosed herein with respect to the vial assembly are intended to similarly apply to the methods disclosed herein, such that a method for preparing or removing the sample can employ or utilize one or more features described with respect to the vial assembly.

According to various embodiments, a frozen sample, e.g. comprising a biological sample such as cells or tissues, can be introduced into a vial assembly disclosed herein. For instance, a predetermined amount of a liquid sample can be poured into the open end of the tubular body. The cap can then be coupled to the open end of the tubular body by rotating the cap such that the threading on the second portion engages at least a portion of the threading on the internal surface of the tubular body. Rotation can be carried out until the cap is snugly fit to the tubular body, for instance, until a bottom surface of the top portion of the cap abuts the lip of the tubular body or abuts a seal disposed between the lip and the top portion of the cap. In this "closed" position, the second portion of the cap can extend into the tubular body cavity containing the liquid sample.

The liquid sample can be added, in various embodiments, in an amount sufficient to at least partially contact the second portion of the cap in the closed position. For instance, the second portion can be at least partially immersed in the liquid sample, e.g., at least about 5% of the second portion can be immersed, such as at least about 10%, 20%, 30%, 40%, 50%, 60%, 70%, 80%, 90%, or even 100% of the second portion is immersed in the liquid sample. According to certain embodiments, the threaded portion of the cap may be a hollow cylindrical shape and the liquid sample may at least partially occupy the internal volume of the threaded portion.

Upon sealing the vial assembly in the closed position, the vial assembly and sample contained therein can be frozen, e.g., at a temperature below the freezing point of the sample. The vial assembly can, for instance, be frozen in an upright position such that the liquid is in contact with a bottom internal surface of the cavity. The vial assembly can also be frozen in an inverted position, such that the liquid is in contact with a top internal surface of the cavity and/or the bottom surface of the top portion of the cap. Regardless of orientation, the sample can be frozen such that the second portion of the cap is at least partially immersed in the liquid sample. The sample thus frozen can take on a complementary shape relative to the second portion of the cap.

Removal of the frozen sample from the vial assembly can be achieved by disengaging the cap from the tubular body. Twisting or rotating of the cap can cause the second portion of the cap in contact with the frozen sample to engage and rotate the frozen sample within the tubular body. The rotating action can serve to loosen the frozen sample from the internal surfaces of the tubular body such that the sample can be more easily ejected from the vial assembly. In additional embodiments, the internal surface of the tubular body may comprise threading extending from the open end to the closed end and the cap may be rotated repeatedly to "unscrew" the sample from the vial, e.g., disengage the sample from the threading in the tubular body. In this embodiment, the second portion of the cap can act in a fashion similar to a screwdriver engaging a top slot of a screw.

According to certain embodiments, the frozen sample can be further dislodged by applying pressure to the closed end of the tubular body, which may be configured, in some embodiments, to compress at least partially upon the application of force. According to various embodiments, the closed end of the tubular body can be compressed by squeezing two or more flanges proximate the closed end. The flanges can apply inward and/or upward force to the bottom of the tubular body to push the frozen sample out of the vial. Alternatively or additionally, the frozen sample can be pulled from the vial using the cap. For example, the second portion of the cap may be equipped with one or more apertures into which the sample has frozen to further engage the second portion with the sample. The attachment between the cap and the frozen sample may allow the user to pull the sample from the vial by displacing the cap from the tubular body for a distance sufficient to fully dislodge the sample.

It will be appreciated that the various disclosed embodiments may involve particular features, elements or steps that are described in connection with that particular embodiment. It will also be appreciated that a particular feature, element or step, although described in relation to one particular embodiment, may be interchanged or combined with alternate embodiments in various non-illustrated combinations or permutations.

It is also to be understood that, as used herein the terms "the," "a," or "an," mean "at least one," and should not be limited to "only one" unless explicitly indicated to the contrary. Thus, for example, reference to "an opening" includes examples having two or more such "openings" unless the context clearly indicates otherwise.

Ranges can be expressed herein as from "about" one particular value, and/or to "about" another particular value. When such a range is expressed, examples include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

All numerical values expressed herein are to be interpreted as including "about," whether or not so stated, unless expressly indicated otherwise. It is further understood, however, that each numerical value recited is precisely contemplated as well, regardless of whether it is expressed as "about" that value. Thus, "a dimension less than 10 mm" and "a dimension less than about 10 mm" both include embodiments of "a dimension less than about 10 mm" as well as "a dimension less than 10 mm."

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a method comprising A+B+C include embodiments where a method consists of A+B+C, and embodiments where a method consists essentially of A+B+C.

It will be apparent to those skilled in the art that various modifications and variations can be made to the present disclosure without departing from the spirit and scope of the disclosure. Since modifications combinations, sub-combinations and variations of the disclosed embodiments incorporating the spirit and substance of the disclosure may occur to persons skilled in the art, the disclosure should be construed to include everything within the scope of the appended claims and their equivalents.

What is claimed is:

1. A vial assembly comprising:
a tubular body comprising a cavity, an open end comprising a lip, and a closed end, wherein an internal surface of the tubular body proximate the open end comprises threading wherein the cavity is configured to store a sample, the sample being in contact with the internal surface of the tubular body; and
a cap configured to couple to the open end of the tubular body, wherein the cap comprises:
a first portion configured to abut the lip of the open end;
a threaded portion configured to couple to at least a portion of the threading on the internal surface of the tubular body;
a second portion protruding from the threaded portion and extending into the cavity of the tubular body,
wherein the tubular body comprises a tube wall and wherein at least a first portion of the tube wall proximate the closed end has a thickness less than a thickness of a second portion of the tube wall proximate the open end;
the tubular body further comprising at least two flanges proximate the closed end of the tubular body, wherein the at least two flanges are configured to hinge inwardly and apply force to the closed end of the tubular body, each of the at least two flanges further comprising at least one gusset configured to apply an upward force to the closed end of the tubular body.

2. The vial assembly of claim 1, wherein the cap is configured to couple to the open end of the tubular body by rotation to engage the threaded portion of the cap to the threading on the internal surface of the tubular body.

3. The vial assembly of claim 1, wherein the tubular body comprises a first portion having an internal surface comprising threading and a second portion having an internal surface not comprising threading.

4. The vial assembly of claim 3, wherein a diameter of the first portion of the tubular body is greater than a diameter of the second portion of the tubular body.

5. The vial assembly of claim 1, wherein the internal surface of the tubular body comprising threading extends from the open end to the closed end of the tubular body.

6. The vial assembly of claim 1, wherein the first portion comprises an upper portion having a height extending above the lip of the open end, the upper portion comprising a textured surface.

7. The vial assembly of claim 1, wherein the first portion is configured to seal the open end of the tubular body.

8. The vial assembly of claim 1, further comprising a sealing member between the first portion and the lip of the tubular body.

9. The vial assembly of claim 1, wherein the threaded portion of the cap comprises a hollow cylinder having an external threaded surface.

10. The vial assembly of claim 1, wherein the second portion comprises a substantially flat shape having at least one dimension chosen from length or width greater than a thickness of the substantially flat shape.

* * * * *